United States Patent
Booth et al.

(10) Patent No.: US 6,458,806 B1
(45) Date of Patent: *Oct. 1, 2002

(54) ARYL ALKENAMIDES DERIVATIVES AS MCP-1 ANTAGONISTS

(75) Inventors: Richard John Booth, Ypsilanti, MI (US); Kenneth Gordon Carson, Needham, MA (US); David Thomas Connor, Ann Arbor, MI (US); Roberta Ellen Glynn, Waltham, MA (US); Bruce David Roth, Plymouth, MI (US); Charles F. Schwender, Glen Gardner, NJ (US); Bharat Kalidas Trivedi, Farmington Hills, MI (US); Paul Charles Unangst, Ann Arbor, MI (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,790

(22) Filed: Aug. 12, 1997

Related U.S. Application Data

(60) Provisional application No. 60/023,966, filed on Aug. 15, 1996.

(51) Int. Cl.$^7$ ............... A61K 31/445; C07D 211/00; C07D 211/02; C07D 211/08
(52) U.S. Cl. ............... 514/315; 514/327; 514/316; 514/317; 514/318; 514/326; 514/331; 546/184; 546/186; 546/187; 546/192
(58) Field of Search ............... 546/184, 192, 546/229, 235, 186, 187; 514/317, 331, 315, 316, 318, 326, 327

(56) References Cited

U.S. PATENT DOCUMENTS

| | | | |
|---|---|---|---|
| 5,017,703 A | * 5/1991 | Matsuo et al. | 546/201 |
| 5,047,417 A | 9/1991 | Minami et al. | 548/336 |
| 5,177,089 A | 1/1993 | Minami et al. | 514/357 |
| 5,312,928 A | 5/1994 | Goldin et al. | 548/495 |
| 5,382,595 A | 1/1995 | Minami et al. | 514/450 |

FOREIGN PATENT DOCUMENTS

| | | |
|---|---|---|
| EP | 0 298 466 | 1/1989 |
| JP | 07-316144 A | 12/1995 |
| WO | WO 95/07291 | 3/1995 |

OTHER PUBLICATIONS

CA 76:153773 (abstract of FR 2068443), 1971.*
Werbel et al., (CA 67:43536, abstract of J.Med. Chem. (1967), 10(3), 366–70, 1967.*
Matsuo et al., (CA 112:76955, abstract of EP 89–100332), 1989.*
Shigenaga et al., CA 124:220093, abstract of Arch. Pharm. (Weinheim, Ger.) (1996), 329(1), pp. 3–10.*
Springer TA "Adhesion receptors of the immune system", Nature, vol. 346, 1990, pp 425–433.
Lawrence MB and Springer TA "Leukocytes Roll on a Selectin at Physiologic Flow Rates: Distinction from and Prerequisite for Adhesion through Integrins", Cell, vol. 65, 1991, pp 859–873.
Butcher EC Leukocyte–Endothelial Cell Recognition: Three (or More) Steps to Specificiy and Diversity, Cell, vol. 67, 1991, pp 1033–1036.
Spangrude GJ et al. "Inhibition of Lymphocyte and Neutrophil Chemotaxis by Pertussis Toxin", The Journal of Immunology, vol. 135, No. 6, 1985, pp 4135–4143.
Nourshargh S and Williams TJ "Evidence that a Receptor–Operated Event on the Neutrophil Mediates Neutrophil Accumulation in vivo", The Journal of Immunology, vol. 145, No. 8, 1990, pp 2633–2638.

(List continued on next page.)

Primary Examiner—Sabiha Qazi
(74) Attorney, Agent, or Firm—Lahive & Cockfield, LLP; Elizabeth A. Hanley, Esq.

(57) ABSTRACT

Aryl alkenamides derivatives of Formula I or a pharmaceutically acceptable salt thereof are novel MCP-1 antagonists and are thus useful in the treatment of inflammation, atherosclerosis, restenosis, and immune disorders such as arthritis and transplant rejection

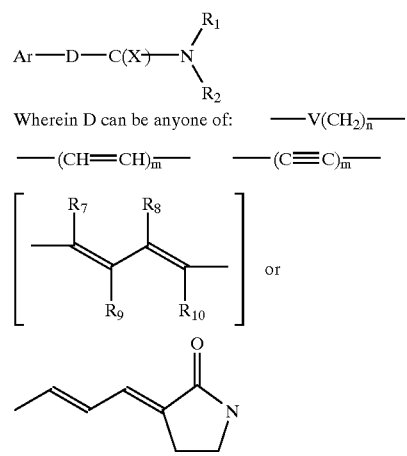

where
V=O, S, NH or a bond;
Ar can be unsubstituted or substituted benzimidazole, phenyl, biphenyl, pyridyl, naphthyl, quinoline or isoquinoline. The other meanings for the terms are recited in the specification below.

15 Claims, 2 Drawing Sheets

OTHER PUBLICATIONS

Sekido N et al. "Prevention of lung reperfusion injury in rabbits by a monoclonal antibody against interleukin–8", Nature, vol. 365, 1993, pp 654–657.

Hechtman DH et al. "Intravascular IL–8: inhibitor of Polymorphonuclear Leukocyte Accumulation at Sites of Acute Inflammation", The Journal of Immunology, vol. 147, No. 3, 1991, pp 883–892.

Huber AR et al. "Regulation of Transendothelial Neutrophil Migration by Endogenous Interleukin–8", Science, vol. 254, 1991, pp 99–102.

Carr MW et al. "Monocyte chemoattractant protein 1 acts as a T–lymphocyte chemoattractant", Proc. Natl. Acad. Sci USA, vol. 91, 1994, pp 3652–3656.

Miller MD and Krangel MS "Biology and Biochemistry of the Chemokines: A Family of Chemotactic and Inflammatory Cytokines", Critical Reviews in Immunology, vol. 12, Nos. 1,2, 1992, pp 17–46.

Springer TA "Traffic Signals for Lymphocyte Recirculation and Leukocyte Emigration: The Multistep Paradigm", Cell, vol. 76, 1994, pp 301–314.

\* cited by examiner

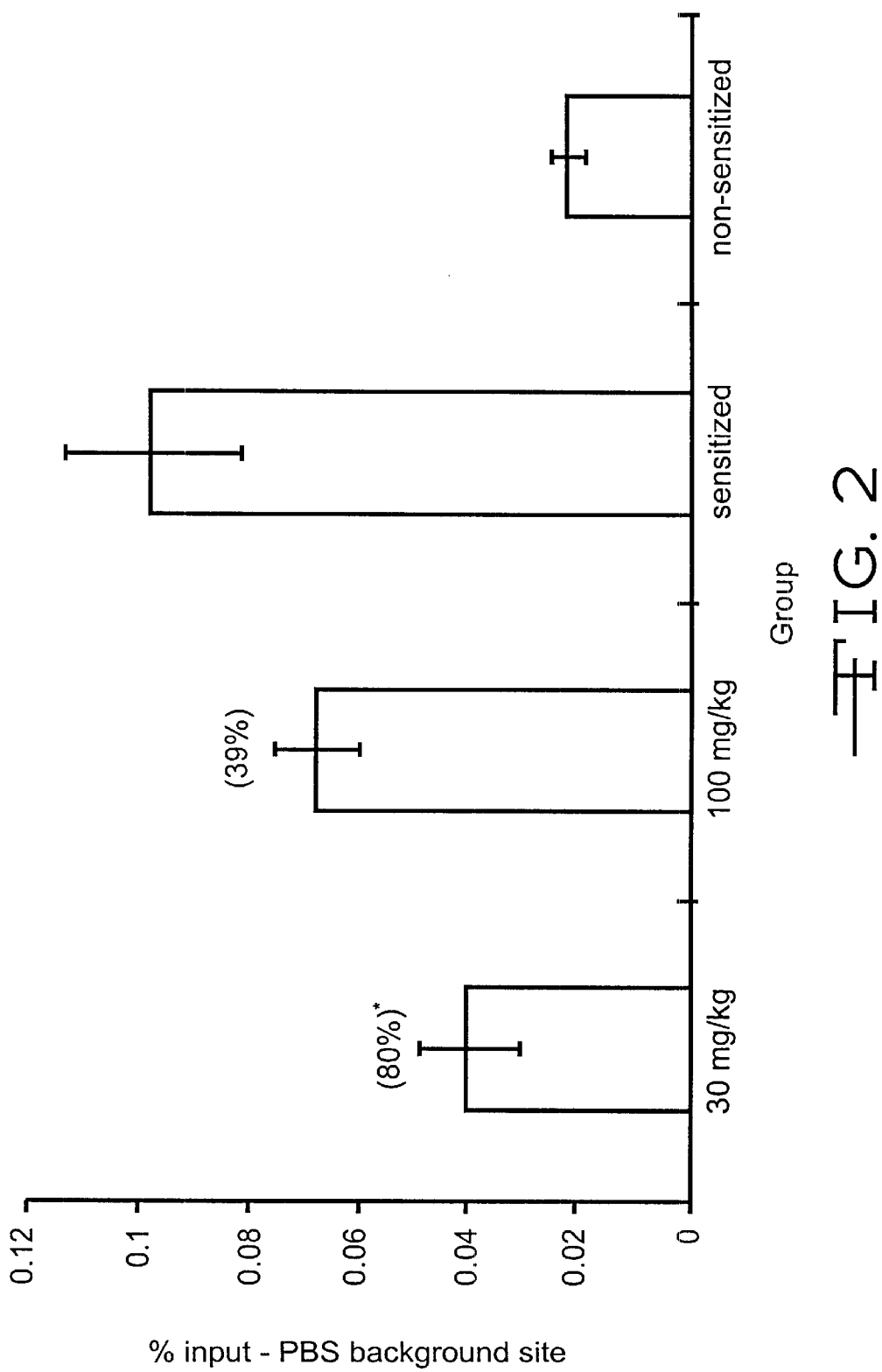

ARYL ALKENAMIDES DERIVATIVES AS MCP-1 ANTAGONISTS

This application claims the benefit of U.S. Provisional Application No. 60/023,966 filed Aug. 15, 1996.

FIELD OF THE INVENTION

The present invention relates to novel compounds and medical methods of treatment of inflammation, atherosclerosis, restenosis, and immune disorders especially those associated with lymphocyte or monocyte accumulation such as arthritis and transplant rejection. More particularly, the present invention concerns the use of aryl alkenamide derivatives.

BACKGROUND OF THE INVENTION

Migration of leukocytes from blood vessels into diseased tissues is important to the initiation of normal disease-fighting inflammatory responses. But this process, known as leukocyte recruitment, is also involved in the onset and progression of debilitating and life-threatening inflammatory and autoimmune diseases. The pathology of these diseases results from the attack of the body's immune system defenses on normal tissues. Thus, blocking leukocyte recruitment to target tissues in inflammatory and autoimmune disease would be a highly effective therapeutic intervention. The leukocyte cell classes that participate in cellular immune responses include lymphocytes, monocytes, neutrophils, eosinophils and basophils. In many cases, lymphocytes are the leukocyte class that initiates, coordinates, and maintains chronic inflammatory responses, and thus are generally the most important class of cells to block from entering inflammatory sites. Lymphocytes attract monocytes to the site, which, collectively with lymphocytes, are responsible for much of the actual tissue damage that occurs in inflammatory disease. Infiltration of lymphocytes and/or monocytes is responsible for a wide range of chronic, autoimmune diseases, and also organ transplant rejection. These diseases include, but are not limited to, rheumatoid arthritis, atherosclerosis, psoriasis, chronic contact dermatitis, inflammatory bowel disease, multiple sclerosis, sarcoidosis, idiopathic pulmonary fibrosis, dermatomyositis, skin pemphigoid and related diseases, (e.g., pemphigus vulgaris, p. foliacious, p. erythematosis), glomerulonephritides, vasculitides, hepatitis, diabetes, allograft rejection, and graft-versus-host disease.

This process by which leukocytes leave the bloodstream and accumulate at inflammatory sites, and initiate disease, takes place in at least three distinct steps which have been described as (1) rolling, (2) activation/firm adhesion and (3) transendothelial migration [Springer, T. A., Nature 346:425–433 (1990); Lawrence and Springer, Cell 65:859–873 (1991); Butcher, E. C., Cell 67:1033–1036 (1991)]. The second step is mediated at a molecular level by chemoattractant receptors. Chemoattractant receptors on the surface of leukocytes bind chemoattractant cytokines secreted by cells at the site of damage or infection. Receptor binding activates leukocytes, increases the adhesiveness of the adhesion molecules that mediate transenadothelial migration, and promotes directed migration of the cells towards the source of the chemoattractant cytokine.

A recent discovery is the existence of a large family (>20 members) of structurally homologous chemoattractant cytokines, approximately 8 to 10 kD in size. These molecules share the ability to stimulate directed cell migration (chemotaxis) and have been collectively called "chemokines" a contraction of chemotactic cytokines. Each chemokine contains four cysteine residues (C) and two internal disulfide bonds. Chemokines can be grouped into two subfamilies, based on whether the two amino terminal cysteine residues are immediately adjacent (C—C family) or separated by one amino acid (C—X—C family). These differences correlate with the organization of the two subfamilies into separate gene clusters. Within each gene cluster, the chemokines typically show sequence similarities between 25 to 60%.

The chemokines of the C—X—C subfamily, such as interleukin-8, are produced by a wide range of cell types and act predominantly on neutrophils as mediators of acute inflammation. Chemokines of the C—C subfamily are also produced by a wide variety of cell types. These molecules act predominantly on subsets of mononuclear inflammatory cells. Currently there are at least seven C—C chemokines with known chemotactic activity for human monocytes and/or T cells, including MCP-1, MCP-2, MCP-3, MCP-4, MIP-1-α, MIP-1β and RANTES. This suggests there may be a high degree of redundancy in chemoattractant pathways. In addition, most C—C chemokines are chemotactic for more than one cell type. For examples, RANTES (regulated on activation, normal T cell expressed and secreted) acts on memory $CD4^+T$ cells, eosinophils, and monocytes. Monocyte chemoattractant protein-1 (MCP-1), another C—C chemokine, acts on monocytes, activated "memory" T cells and on basophils. MCP-1 is also a potent secretogogue of inflammatory mediators from monocytes and basophils.

Five C—C chemokine receptors have recently been characterized (CKR1–5 or CCR1–CCR5), and all of these belong to the seven transmembrane spanning G protein-coupled receptor family. Each of these receptors mediates the binding and signalling of more than one chemokine. For example, the CCR1 receptor binds both MIP-1α and RANTES. There are 2 receptors which bind MCP-1, CCR2 (with alternately spliced forms, 2A and 2B) and CCR4. CCR2 is also known to mediate binding and signaling of MCP-3. The CCR4 receptor binds and signals, in addition to MCP-1, with RANTES and MIP-1a. Which of these is responsible for the MCP-1 mediated recruitment of monocytes and T cells is not known.

In agreement with the observation that lymphocyte emigration into inflammatory sites is usually accompanied by emigration of monocytes, MCP-1 is expressed at sites of antigen challenge and autoimmune disease. However, analyses of human inflammatory lesions with antibodies to other chemokines show RANTES, MIP-1α, MIP-1β and MCP-3 to be present as well. Injection of MCP-1 into skin sites in mice provokes only a mild monocytic infiltrate or no infiltrate at all (Ernst, C. A. et al., J. Immunol. 152:3541–3544, 1994). Whether these results reflect redundant and complex recruitment pathways has not been resolved. MCP-1 and MCP-3 may play a role in allergic hypersensitivity disease. This is suggested by the observation that MCP-1 lacking the amino terminal glutamic acid loses the ability to stimulate basophil mediator release and acquires activity as an eosinophil chemoattractant.

Chemokines of both subfamilies may bind to heparan sulfate proteoglycans on the endothelial cell surface, and may function principally to stimulate haptotaxis of leukocytes that attach to cytokine-activated endothelium through induced adhesion molecules. Additionally, the MCP-1 has been reported to selectively activate the β1 integrin family of leukocyte adhesion molecule, suggesting a role in leukocyte interactions with the extracellular matrix. Hence, MCP-1 may not only trigger the initial arrest and adhesion of monocytes and T cells, but may also act to guide their migration in extravascular space, where β₁ integrins primarily function.

Chemoattractants appear to be required for transendothelial migration in vitro and in vivo and can induce all steps required for transmigration in vivo. Injection of neutrophil chemoattractants into skin or muscle leads to robust emigration of neutrophils from the vasculature and accumulation at the injection site (Colditz, 1991). Pretreatment of neutrophils with pertussis toxin inhibits emigration into inflammatory sites (Spangrude, et al., 1985; Nourshargh and Williams, 1990). Moreover, MAb to IL-8 markedly inhibits neutrophil emigration in inflammation (Sekido et al., 1993).

Neutrophil chemoattractants injected into the same skin site hours apart will stimulate neutrophil accumulation the first time but not the second time, whereas a second injection into a distant site will stimulate accumulation at that site. This desensitization occurs for homologous chemoattractants only (Colditz, 1991) or those that interact with the same receptor. Thus, chemoattractants can act on and homologously desensitize a cell type that is localized in tissue.

Chemoattractants impart directionality to leukocyte migration. By contrast with intradermal injection, intravascular injection of IL-8 does not lead to emigration (Hechtman et al., 1991). Cytokine-stimulated endothelial monolayers grown on filters secrete IL-8 into the underlying collagen layer. Neutrophils added to the apical compartment emigrate into the basilar compartment, but not when the IL-8 gradient is disrupted by addition of IL-8 to the apical compartment (Huber et al., 1991).

The endothelium may present chemoattractants to leukocytes in a functionally relevant way, as well as providing a permeability barrier that stabilizes the chemoattractant gradient. Since leukocytes, responding to specific antigen or inflammatory signals in tissue, may signal emigration of further leukocytes into the site, a chemoattractant was sought in material secreted by mitogen-stimulated mononuclear cells (Carr et al. 1994). Purification to homogeneity guided by a transendothelial lymphocyte chemotaxis assay revealed that nonocyte chemoattractant protein 1 (MCP-1), previously thought to be solely a monocyte chemoattractant, is a major lymphocyte chemoattractant. An activated subset of memory lymphocytes respond to MCP-1. In the same assay, lymphocytes respond to RANTES and MIP-la but less so than to MCP-1 (C—C chemokines) and not at all to IL-8 or IP-10 (C—X—C chemokines). This physiologically relevant assay suggests that C—C chemokines tend to attract both monocytes and lymphocytes. In agreement with the observation that lymphocyte emigration into inflammatory sites is accompanied by emigration of monocytes, MCP-1 is abundantly expressed at sites of antigen challenge and autoimmune disease (Miller and Krangel, 1992) and, together with other chemokines, is an excellent candidate to provide the step 2 signal required to activate integrin adhesiveness and emigration of lymphocytes in vivo. (Traffic Signals for Lymphocyte Recirculation and Leukocyte Emigration: The Multistep Paradigm; Springer, 1994, *Cell* 76: 301–314).

We have surprisingly found that aryl alkenamide derivatives are MCP-1 receptor antagonists and are capable of inhibiting the binding of MCP-1 to its receptor. Surprisingly, the compounds block T cell migration in vitro, and more surprisingly still, have dramatic effects on the recruitment of inflammatory cells in multiple models of inflammatory diseases. Thus, these compounds are useful as agents for the treatment of inflammatory disease, especially those associated with lymphocyte and/or monocyte accumulation, such as arthritis, atherosclerosis and transplant rejection. In addition, these compounds can be used in the treatment of allergic hypersensitivity disorders such as asthma and allergic rhinitis characterized by basophil activation and eosinophil recruitment, as well as for the treatment of restenosis and chronic or acute immune disorders.

SUMMARY OF THE INVENTION

Accordingly, a first embodiment of the present invention provides a method of treatment of chronic or acute inflammatory disease, atherosclerosis, restenosis, chronic or acute immune disorders, and transplant rejection in a mammal in need thereof comprising administering to such mammal an effective amount of a compound of Formula I or a pharmaceutically acceptable salt thereof:

FORMULA I

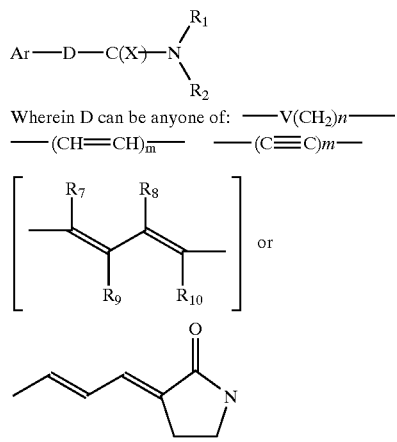

V=O, S, NH or a bond;
Ar can be unsubstituted or substituted benzimidazole, phenyl, biphenyl, pyridyl, naphthyl, quinoline, isoquinoline or indole;
n=2–6;
m=1–3;
X=O (oxygen), S (sulfur), =CH₂, =NH or H₂;
R₁ and R₂ can independently be hydrogen, lower alkyl of from 1–4 carbon atoms,
—(CH₂)ₙOR₆,
—(CH₂)ₙNR₃R₄,
—(CH₂)ₙ'CONR₃R₄,
—(CH₂)ₙ'COOR₆,
—(CH₂)ᵣAr',
where
n'=0–6
r=0–4
R₃ and R₄ can independently be hydrogen,
lower alkyl of from 1–4 carbon atoms, —(CH₂)ₙR₆, or —(CH₂)ₘ—Ar', which can be unsubstituted or substituted with up to 3 substitutents, where "Ar'" is phenyl, pyridyl, or indole;
R₃ and R₄ may also be taken together to form a cyclic ring of 3–8 atoms which may also contain oxygen or the group NR₅ where R₅ can be
hydrogen,
lower alkyl of from 1–4 carbon atoms,
cycloalkyl of from 5–12 carbon atoms, or
—(CH₂)ₘ-Phenyl, which can be unsubstituted or substituted with up to 3 substitutents;

$R_6$ can be
hydrogen,
lower alkyl or $(CH_2)_m$-Phenyl;
m=1–3;
$R_1$ and $R_2$ may be also taken together to form a ring of 3–8 atoms which may also contain oxygen or the group $NR_5$, which ring may be substituted on one or more carbon atoms with the group $NR_3R_4$;
the subtituents are defined as:
halogen,
nitro,
$CF_3$,
alkyl of from 1–12 carbon atoms;
—$(CH_2)_rOR6$
—$(CH_2)_rNR_3R_4$
—$(CH_2)_rCNR_3R_4$
—$(CH_2)_rC(O)OR_6$ or
—$(CH_2)_r$—$SO_2$—$OR_6$;
$R_7$, $R_8$, $R_9$ and $R_{10}$ can each independently be hydrogen, lower alkyl or aryl;
and $R_7$ and $R_8$ or $R_9$ and $R_{10}$ or X or $R_2$ when taken together can form a 5–7 membered ring including cycloalkyl, cycloalkenyl, aryl, or heteroaryl containing nitrogen, oxygen or sulfur.

A still further or second embodiment of the present invention is a method of treatment of atherosclerosis in mammals in need thereof comprising administering to such mammal an effective amount of a compound selected from the group consisting of: a compound of formula I in combination with one or more agents selected from the group consisting of:

(a) ACAT inhibitor;
(b) HMG-CoA reductase inhibitor;
(c) Lipid regulator; and
(d) Bile acid sequestrant;

or a pharmaceutically acceptable salt thereof.

Also, the invention is directed to inhibiting the binding of MCP-1 to an MCP-1 receptor (i.e., one or more MCP-1 receptors) by utilizing effective inhibiting amounts of a compound of Formula I.

Also, the invention is directed to the novel compositions of Formula I.

Finally, the present invention is directed to a pharmaceutical composition for administering an effective amount of a compound of Formula I in unit dosage form in the treatment methods mentioned above.

BRIEF DESCRIPTION OF DRAWINGS

FIG. 2 is a graphic illustration of the degree of inhibition of T cell recruitment in rat DHR over a 24 hour period at various doses of compund 1. There was a statisticallly significant inhibitory effect of the compound when administered at 30 mg/kg per os at the time of antigen challenge.

DETAILED DESCRIPTION OF THE INVENTION

Figure 1:
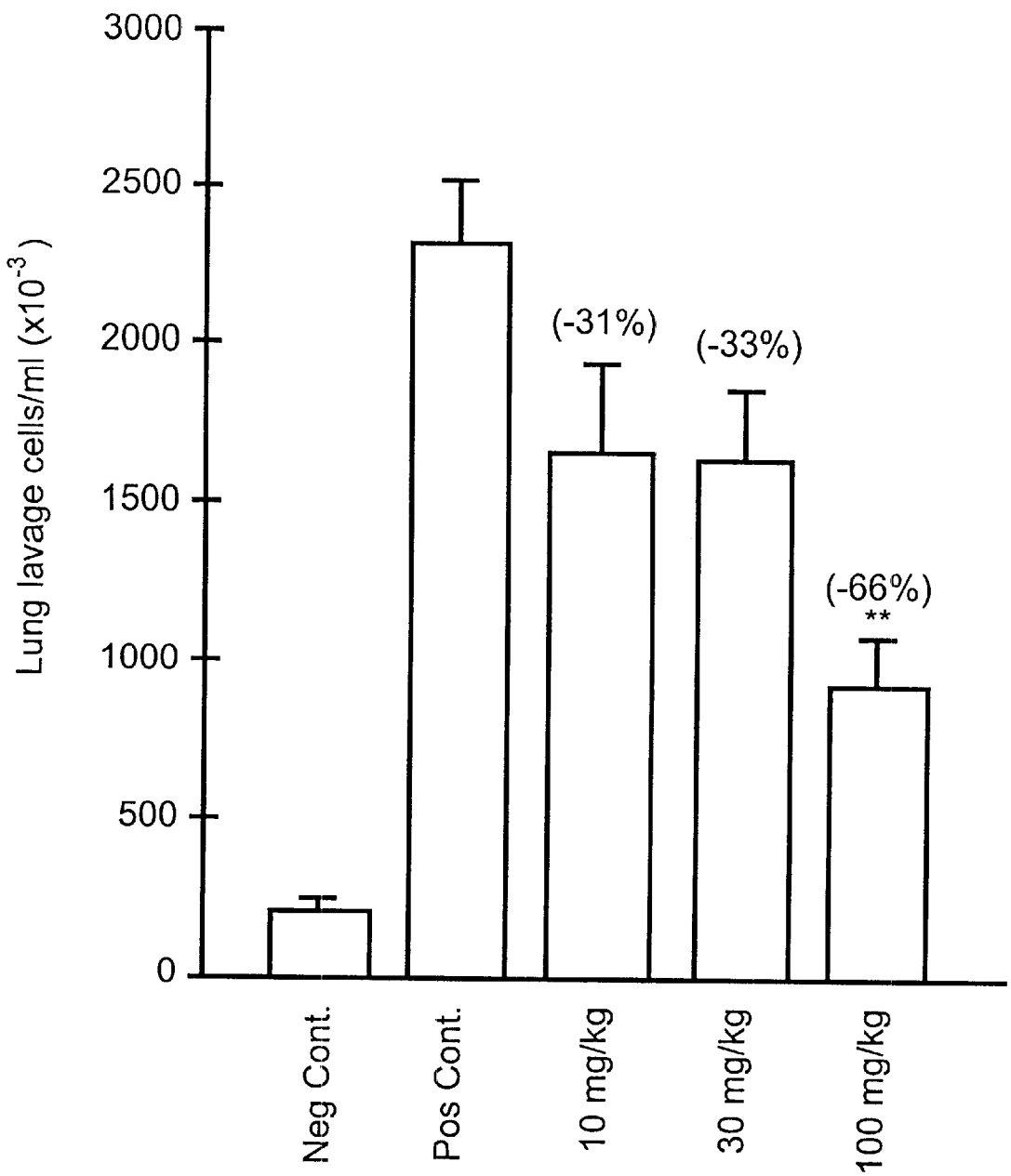
FIG. 1 shows the dose response of Example 1 in a rat glucan vasculitis assay.

In the compounds of Formula I, the term "lower alkyl" means a straight or branched hydrocarbon radical having from 1 to 4 carbon atoms and includes, for example, methyl, ethyl, n-propyl, isopropyl, n-butyl, sec-butyl, isobutyl and tert-butyl.

The term "lower alkoxy" is O-alkyl as defined above for lower alkyl.

"Halogen" is fluorine, chlorine, bromine, or iodine.

Heterocycle is defined as five or six-membered mono or bicyclic ring structure which may contain one or more heteroatoms such as N, O or S; examples of heterocycle are pyridine, thiophene, pyrimidine, pyridazine, pyrazole, thiazole, oxazole, indole, N-alkylindole, quinoline, quinazoline, quinazolinone and the like. Substitutents can be hydrogen, alkyl of from 1–4 carbon atoms; cycloalkyl of from 5–7 carbon atoms, $OR_6$, $SR_6$, —$NR_3R_4$, $(CH_2)_n$—$NR_3R_4$, —$COOR_6$, —$CH_6OR_6$, —$CON_3R_4$, —$COR_6$, —$CH_2CONR_3R_4$, $SO_2R_3R_4$, $NHCOR_6$, $NR_6$, $CONR_6$ where $R_3$, $R_4$ and $R_6$ are as defined above; —CN or halogen.

The term "mammal" includes animals and humans.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds 4 can be prepared by contacting the free base form with a sufficient amount of the desired acid to produce the salt in the conventional manner. The free base form may be regenerated by contacting the salt form with a base and isolating the free base in the conventional manner. The free base forms may differ from their respective salt forms somewhat in certain physical properties such as solubility in polar solvents.

Pharmaceutically acceptable base addition salts are formed with metals or amines, such as alkali and alkaline earth metals or organic amines. Examples of such metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds can be prepared by contacting the free acid form with a sufficient amount of the desired base to produce the salt in the conventional manner. The free acid form may be regenerated by contacting the salt form with an acid and isolating the free acid in the conventional manner. The free acid forms can differ from their respective salt forms somewhat in certain physical properties such as solubility in polar solvents.

Certain of the compounds of the present invention can exist in unsolvated forms as well as solvated forms, including hydrated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of the first embodiment used in the method of the present invention is a compound formula I of:

FORMULA I

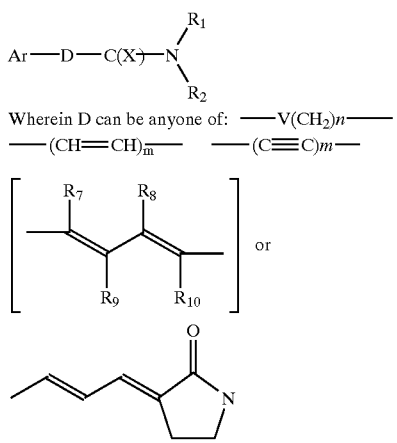

V=O, S, NH or a bond;
Ar can be unsubstituted or substituted benzimidazole, phenyl, biphenyl, pyridyl, naphthyl, quinoline, isoquinoline or indole;
n=2–6;
m=1–3;
X=O (oxygen), S (sulfur), =CH$_2$, =NH or H$_2$;
R$_1$ and R$_2$ can independently be hydrogen,
lower alkyl of from 1–4 carbon atoms,
—(CH$_2$)$_n$OR$_6$,
—(CH$_2$)$_n$NR$_3$R$_4$,
—(CH$_2$)$_n$'CONR$_3$R$_4$,
—(CH$_2$)$_n$'COOR$_6$,
—(CH$_2$)$_r$Ar',
where
n'=0–6
r=0–4
R$_3$ and R$_4$ can independently be hydrogen,
lower alkyl of from 1–4 carbon atoms, —(CH$_2$)$_n$OR$_6$, or —(CH$_2$)$_m$—Ar', which can be unsubstituted or substituted with up to 3 substitutents, where "Ar'" is phenyl, pyridyl, or indole;
R$_3$ and R$_4$ may also be taken together to form a cyclic ring of 3–8 atoms which may also contain oxygen or the group NR$_5$ where R$_5$ can be
hydrogen,
lower alkyl of from 1–4 carbon atoms,
cycloalkyl of from 5–12 carbon atoms, or
—(CH$_2$)$_m$-Phenyl, which can be unsubstituted or substituted with up to 3 substitutents;
R$_6$ can be
hydrogen,
lower alkyl or (CH$_2$)$_m$-Phenyl;
m=1–3;
R$_1$ and R$_2$ may be also taken together to form a ring of 3–8 atoms which may also contain oxygen or the group NR$_5$, which ring may be substituted on one or more carbon atoms with the group NR$_3$R$_4$;

the substitutents are defined as:
halogen,
nitro,
CF$_3$,
alkyl of from 1–12 carbon atoms;
—(CH$_2$)$_r$OR$_6$
—(CH$_2$)$_r$NR$_3$R$_4$
—(CH$_2$)$_r$CONR$_3$R$_4$
—(CH$_2$)$_r$C(O)OR$_6$ or
—(CH$_2$)$_r$—SO$_2$—OR$_6$;
R$_7$, R$_8$e R$_9$ and R$_{10}$ can each independently be hydrogen, lower alkyl or aryl;
and R$_7$ and R$_8$ or R$_9$ and R$_{10}$ or X or R$_2$ when taken together can form a 5–7 membered ring including cycloalkyl, cycloalkenyl, aryl, or heteroaryl containing nitrogen, oxygen or sulfur.

Examples of some desirable compounds are as follows:

wherein

R =

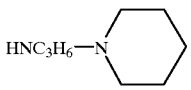 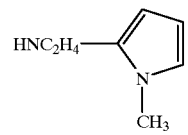

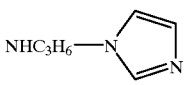 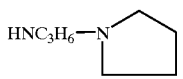

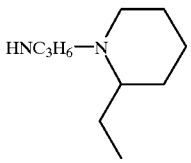 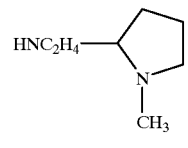

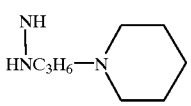

 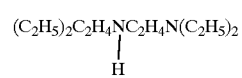

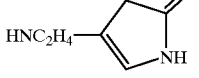

HNC$_3$H$_6$N(CH$_3$)$_2$

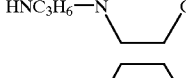 

HNC$_3$H$_6$N(C$_2$H$_5$)$_2$ (CH$_3$)$_2$NC$_3$H$_6$NC$_3$H$_6$N(CH$_3$)$_2$
H

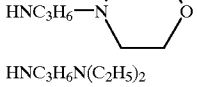 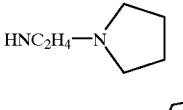

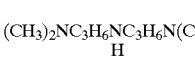 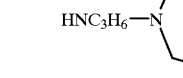

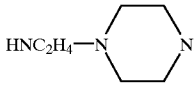 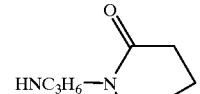

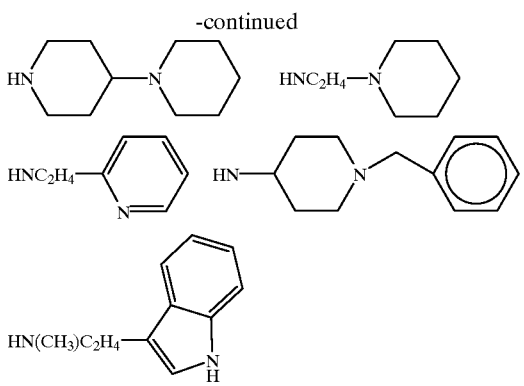

An aryl alkenamide can be administered to a mammal (e.g., a human) alone or in conjunction with (before, along with or subsequent to) one or more other such compounds or another agent to be administered.

Preferred compounds used in the second embodiment of the present invention include one or more agents selected from the group consisting of an acyl CoA:cholesterol acyltransferase (ACAT) inhibitor; 3-hydroxy-3-methylglutaryl-coenzyme A reductase (HMG-COA reductase) inhibitor; lipid regulator; and bile acid sequestrant.

Examples of ACAT inhibitors include DL-melinamide disclosed in British Patent 1,123,004 and *Japan. J. Pharmacol.*, 1986;42:517–523; 2,2-dimethyl-N-(2,4,6-trimethoxyphenyl)dodecanamide disclosed in U.S. Pat. No. 4,716,175; N-[2,6—bis(1-methylethyl)phenyl]-N'-[[1-(4-dimethylaminophenyl)cyclopentyl]methyl]urea disclosed in U.S. Pat. No. 5,015,644; 2,6-bis(1-methylethyl)phenyl-[[2,4,6-tris(1-methylethyl)phenyl]acetyl]sulfamate disclosed in copending U.S. patent application Ser. No. 08/233,932 filed Apr. 13, 1994; and the like. U.S. Pat. Nos. 4,716,175 and 5,015,644 and U.S. patent application Ser. No. 08/233,932 and British Patent 1,123,004 and *Japan. J. Pharmacol.*, 1986;42:517–523 are hereby incorporated by reference.

Examples of HMG-CoA reductase inhibitors include lovastatin disclosed in U.S. Pat. No. 4,231,338; pravastatin disclosed in U.S. Pat. No. 4,346,227; simvastatin disclosed in U.S. Pat. No. 4,444,784; fluvastatin disclosed in U.S. Pat. No. 4,739,073; atorvastatin disclosed in U.S. Pat. Nos. 4,681,893 and 5,273,995; and the like. U.S. Pat. Nos. 4,231,938; 4,346,227; 4,444,784; 4,681,893; 4,739,073 and 5,273,995 are hereby incorporated by reference.

Examples of bile acid sequestrants include colestipol disclosed in U.S. Pat. Nos. 3,692,895 and 3,803,237; cholestyramine disclosed in U.S. Pat. No. 3,383,281 and Casdorph R. in *Lipid Pharmacology.*, 1976;2:222–256, Paoletti C., Glueck J., eds. Academic Press, NY; and the like. U.S. Pat. Nos. 3,692,895; 3,803,237 and 3,383,281 and R. Casdorph, supra, 1976, are hereby incorporated by reference.

Examples of lipid regulators include gemfibrozil described in U.S. Pat. No. 3,674,836; bezafibrate disclosed in U.S. Pat. No. 3,781,328; clofibrate disclosed in U.S. Pat. No. 3,262,850; fenofibrate disclosed in U.S. Pat. No. 4,058,552; niacin disclosed in McElvain, et al., *Org. Syn.*, 1925;4:49; and the like. U.S. Pat. Nos. 3,674,836; 3,781,328; 3,262,850 and 4,058,552 and McElvain, et al., *Org. Syn.*, 1925;4:49 are hereby incorporated by reference.

Methods of preparing ACAT inhibitors, HYG-CoA reductase inhibitors, lipid regulators, and bile acid sequestrants used in the second embodiment of the present invention are disclosed in the aforementioned references.

The invention is also concerned with novel compounds as aryl alkenamide derivatives:

A compound of formula I

FORMULA I

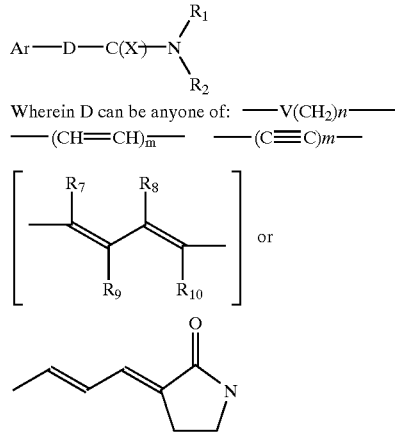

Wherein D can be anyone of: —V(CH$_2$)$n$—
—(CH=CH)$\overline{m}$— —(C≡C)$m$—

$$\left[ \begin{array}{c} R_7 \quad R_8 \\ \diagup\!\!\diagdown\!\!\diagup\!\!\diagdown \\ R_9 \quad R_{10} \end{array} \right] \text{ or }$$

V=O, S, NH or a bond;
Ar can be unsubstituted or substituted benzimidazole, phenyl, biphenyl, pyridyl, naphthyl, quinoline, isoquinoline or indole;
n=2–6;
m=1–3;
X=O (oxygen), S (sulfur), =CH$_2$, =NH or H$_2$;
R$_1$ and R$_2$ can independently be hydrogen,
lower alkyl of from 1–4 carbon atoms,
—(CH$_2$)$_n$OR$_6$,
—(CH$_2$)$_n$NR$_3$R$_4$,
—(CH$_2$)$_n$'CONR$_3$R$_4$,
—(CH$_2$)$_n$'COOR$_6$,
—(CH$_2$)$_r$Ar',
where
n'=0–6
r=0–4
R$_3$ and R$_4$ can independently be hydrogen,
lower alkyl of from 1–4 carbon atoms, —(CH$_2$)$_n$OR$_6$, or
—(CH$_2$)$_m$—Ar', which can be unsubstituted or substituted with up to 3 substitutents, where "Ar$^1$" is phenyl, pyridyl, or indole;
R$_3$ and R$_4$ may also be taken together to form a cyclic ring of 3–8 atoms which may also contain oxygen or the group NR$_5$ where R$_5$ can be
hydrogen,
lower alkyl of from 1–4 carbon atoms,
cycloalkyl of from 5–12 carbon atoms, or
—(CH$_2$)$_m$-Phenyl, which can be unsubstituted or substituted with up to 3 substitutents;
R$_6$ can be
hydrogen,
lower alkyl or (CH$_2$)$_m$-Phenyl;
m=1–3;
R$_1$ and R$_2$ may be also taken together to form a ring of 3–8 atoms which may also contain oxygen or the group NR$_5$, which ring may be substituted on one or more carbon atoms with the group NR$_3$R$_4$;
the subtituents are defined as:
halogen,
nitro,
CF$_3$,
alkyl of from 1–12 carbon atoms;
—(CH$_2$)$_r$OR$_6$
—(CH$_2$)$_r$NR$_3$R$_4$
—(CH$_2$)$_r$CONR$_3$R$_4$
—(CH$_2$)$_r$C(O)OR$_6$ or
—(CH$_2$)$_r$—SO$_2$—OR$_6$;
R$_7$, R$_8$, R$_9$ and R$_{10}$ can each independently be hydrogen, lower alkyl or aryl;

and $R_7$ and $R_8$ or $R_9$ and $R_{10}$ or X or $R_2$ when taken together can form a 5–7 membered ring including cycloalkyl, cycloalkenyl, aryl, or
heteroaryl containing nitrogen, oxygen or sulfur,
with the proviso that when
D=—[CH=CH]$_2$—
$R_1$=H
$R_2$=—(CH$_2$)$_n$NR$_3$R$_4$ and
X=O, then
Ar can not be phenyl or substituted phenyl.

General Synthesis:

Compounds of Formula I can be synthesized as shown in Scheme A, see J. Med Chem 1967, Vol. 10:366–370:

SCHEME A

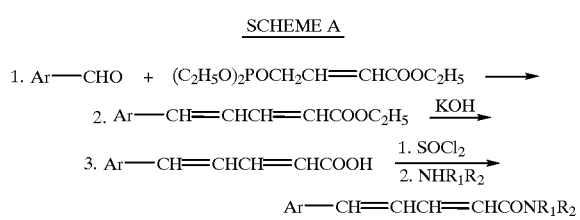

Alternatively, compounds of Formula I can be synthesized as shown in following schemes:

SCHEME B

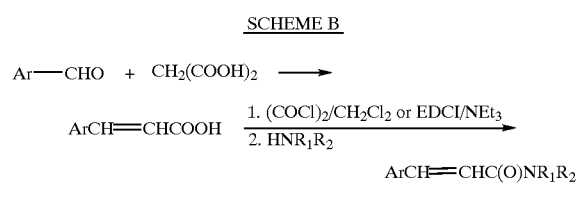

SCHEME C

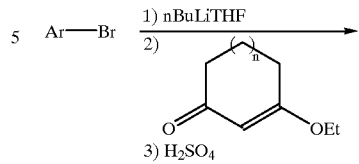

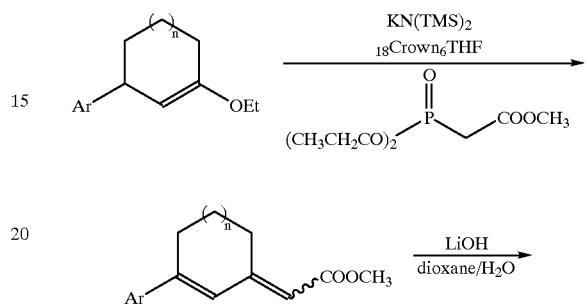

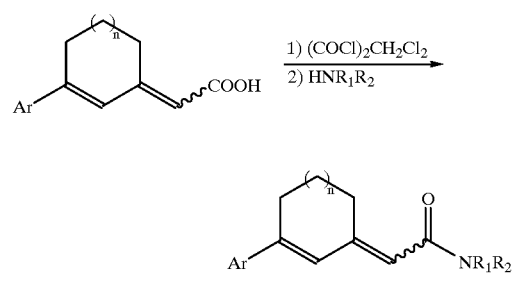

SCHEME D

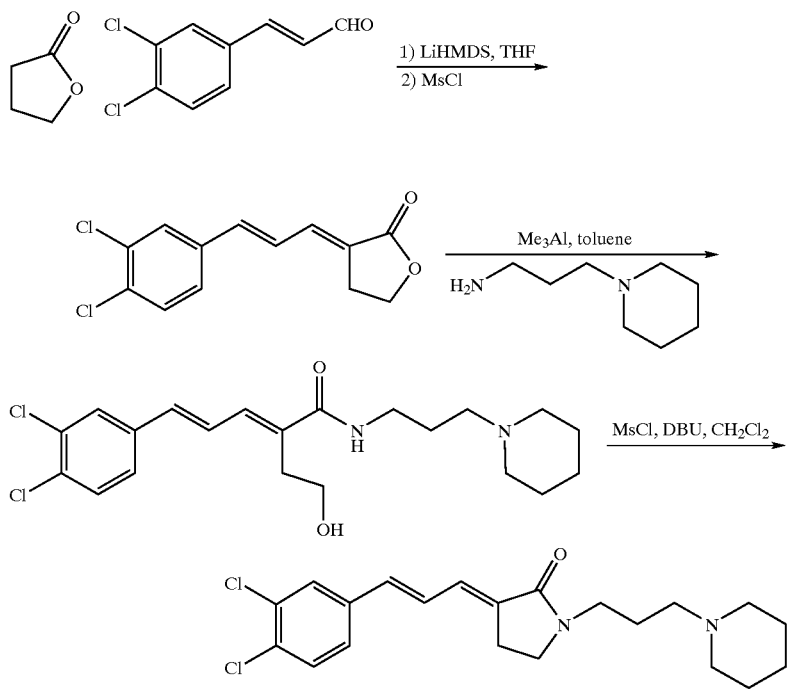

SCHEME E

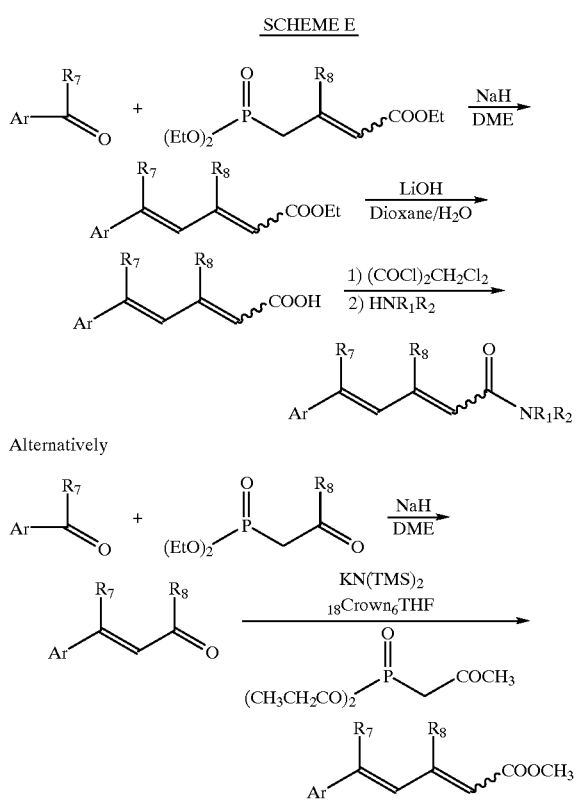

Alternatively

SCHEME F

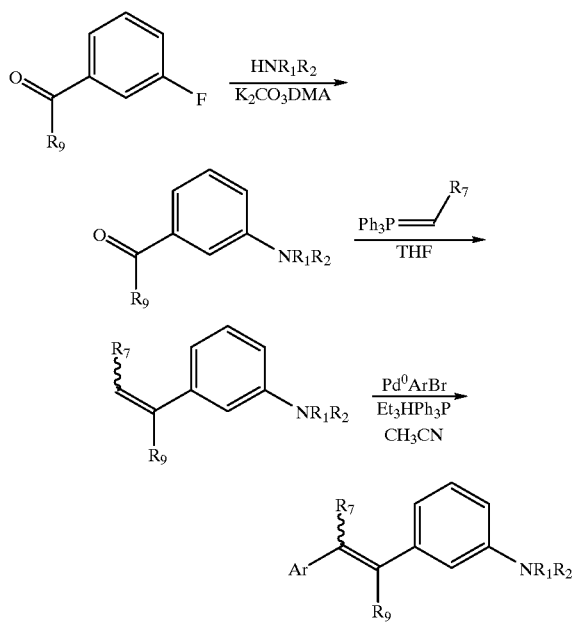

Preparation of Example 18

Step A: Preparation of Ethyl 5-(3,4-dichlorophenyl)-3-methyl-pentadienoate.

A suspension of sodium hydride (0.40 g, 10.0 mmol) in anhydrous dimethoxyethane (5 mL) is cooled in a room temperature water bath. While stirring vigorously, triethyl-3-methyl-4-phosphonocrotonate (2.64 g, 10 mmol), is added dropwise over 10 minutes. After gas evolution has stopped, (~5 minutes) the reaction mixture is treated with a solution of 3,4-dichlorobenzaldehyde (1.75 g, 10 mmol) in anhydrous dimethoxyethane (5 mL). The resulting brown solution is then heated to reflux. After three hours, the mixture is cooled and quenched with saturated aqueous brine. The aqueous layer is extracted several times with EtOAc, and the combined organic layers are dried (sodium sulfate) and concentrated in vacuo. The resulting brown oil is chromatographed on silica gel eluting with 7% EtOAc: 93% hexane to give 1.146 g of a brown oil, which is a 1:1 mixture of alkene isomers at C-2.

Step B: Preparation of 5-(3,4-dichlorophenyl)-3-methyl-pentadienoic Acid.

A solution of ehtyl 5-(3,4-dichlorophenyl)-3-methyl-pentadienoate (0.120 g, 0.418 mmol) in tetrahydrofuran (0.5 mL) is treated with aqueous 1 M lithium hydroxide (0.5 mL, 0.5 mmol). The cloudy reaction mixture is treated with dioxane (1 mL). After stirring at room temperature for two days, the mixture is concentrated in vacuo. The residue is diluted with 1 M aqueous HCl and extracted several times with chloroform. The organic layers are combined, dried (sodium sulfate), and concentrated in vacuo to yield 0.110 g of a white solid, mp, 212–214° C.

Step C: Preparation of N-piperidinopropyl-5-(3,4-dichlorophenyl)-3-methyl-pentadiene carboxamide A suspension of 5-(3,4-dichlorophenyl)-3-methyl-pentadienoic acid (0.100 g, 0.390 mmol) in $CH_2Cl_2$ (5 mL) is treated with triethyl-amine (0.050 cr, 0.050 mmol) and cooled to 0° C. The resulting colorless solution is then treated with isobutyl chloroformate (0.065 g, 0.050 mmol). After 30 min., piperidino-propylamine (0.071 g, 0.050 mmol) is added, and the reaction mixture is allowed to warm to room temperature. After stirring overnight, the reaction mixture is quenched with aqueous sodium bicarbonate. The aqueous layer is extracted several times with $CH_2Cl_2$, and the combined organic layers are dried (sodium sulfate), and concentrated in vacuo. The residue is treated with excess methanolic HCl, evaporated in vacuo, and rinsed with ether to yield 0.159 g of a hygroscopic white solid, mp 50–60° C.

The compounds are valuable agents for the treatment of inflammatory diseases or conditions, atherosclerosis, restenosis, and autoimmune disorders such as arthritis and transplant rejection. In a preferred embodiment, the disease or condition is one which is associated with lymphocyte and/or monocyte infiltraion of tissues (including recruitment and/or accumulation in tissues), such as arthritis (e.g., rheumatoid arthritis), inflammatory bowel diseases (e.g., Crohn's disease, ulcerative colitis), multiple sclerosis, idiopathic pulmonary fibrosis, and graft rejection (e.g., in transplantation), including allograft rejection or graft-versus-host disease. In addition, diseases characterized by basophil activation and/or eosinophil recruitment, including allergic hypersensitivity disorders such as asthma. and allergic rhinitis can be treated according to the present invention.

Other diseases that may be treated with the compounds of Formula I are:

psoriasis, chronic contact dermatitis, sarcoidosis, dermatomyositis, skin phemphicgoid and related diseases (e.g., pemphigus vulgaris, p. foliacious, p. arythhematosis), glomerulonephritides, vasculitides (e.g., necrotizing, cutaneous, and hypersensitivity vasculitis), hepatitis, diabetes, systemic lupus erythematosus and myasthenia gravis.

In addition to psoriasis, other inflammatory dermatoses such as dermatitis, eczema, atopic dermatitis, allergic contact dermatitis, urticaria and reperfusion injury may also be treated.

The data in the table show the MCP-receptor binding activity of representative aryl compounds of the present invention.

MCP-1 Binding Assay

Membranes used in the MCP-1 binding assay were prepared from THP-1 cells (human monocytic cell line source—American Type Culture Collection, Tumor Immunology Bank #202, Rockville, Md., accession no. ATCC TIB 202). Cells were harvested by centrifugation and washed twice in ice-cold PBS (phosphate-buffered saline) and the cell pellet was frozen at −80° C. in some cases. Cells were resuspended in ice-cold lysis buffer 5mM HEPES (2-(4N-, [2-hydroxyethyl] piperazin-1-yl)-N'-(2-ethanesulfonic acid), pH 7.5, 2 mM EDTA (ethylenediaminetetraacetic acid), 5 ug/ml each leupeptin, aprotinin, chymostatin (protease inhibitors), and 100 ug/ml PMSF (phenylmethane sulfonyl fluoride—also a protease inhibitor)) at a concentration of 5×10$^7$ cells/ml. The cell suspension was dounced 10–15 times using the B pestle (small pestle of tissue grinder—clearance is 0.07 mm; source—Fisher Scientific) on ice. Nuclei and debris were removed by centrifugation at 500–1000×g for 10 minutes at 4° C. The supernatant was transferred to a fresh tube and centrifuged at 25,000×g for 30 minutes at 4° C. The supernatant was aspirated and the pellet was resuspended in freezing buffer (10 mM HEPES, pH 7.5, 300 mM sucrose, 1 ug/ml each leupeptin, aprotinin, chymostatin, and 10 ug/ml PMSF) using a minihomogenizer until all clumps were resolved. Membranes were aliquoted and frozen at minus 70–85° C. until needed. Typical binding assays used 10–20 ug/well of total membrane protein as determined with a standard protein assay (e.g. BioRad, Richmond, Calif.).

For binding, 10–20 ug total membrane protein were included in the binding reaction along with 0.2 nM I$^{125}$-labeled MCP-1 (Amersham, Arlington Heights, Ill.) with or without unlabeled competitor MCP-1 (Peprotech, Rocky Hill, N.J.) (at 250–500 nM). Binding reactions were performed in a final volume of 100 ul in a binding buffer containing 10 mM HEPES, pH 7.2, 1 mM CaCl$_2$, 5 mM MgCl$_2$, 0.5% BSA (bovine serum albumin). After 30–60 minutes at room temperature, the binding reactions were filtered through GF/C filters (Whatman glass fiber filters, Type C) or GF/B unifilter plates (Packard) which had been pre-soaked with 0.3% polyethyleneimine and washed twice with binding buffer containing 0.5 M NaCl. Filters were dried and counted in a Beta-Plate scintillation counter using standard scintillation fluid. Final concentration of compound in the binding assay ranged from 0.05–100 μM. Compounds were dissolved in DMSO (dimethyl sulfoxide). Final concentrations of DMSO in the binding were kept constant at 0.5%.

IC50s were calculated using a non-linear 3-parameter logistic curve fit. IC50 means the concentration at which 50% inhibition is achieved. Negative controls contained the same amount of DMSO vehicle as used in wells containing compound. Positive control contained 250–500 nM unlabeled competitor MCP-1 in DMSO vehicle. Non-specific binding (the level of bound $^{125}$I-label MCP-1 in the presence of 250–500 μM unlabeled MCP-1) was subtracted from all data prior to analysis.

The data in the table below show the MCP-receptor binding activity of representative benzimidazoles of the present invention.

$$Ar—D—C(O)NR_1R_2$$

TABLE I

MCP-1 BINDING ASSAY

| Ex | R$_1$ | R$_2$ | D | Ar | Inhibition Of MCP-1 Binding IC$_{50}$ μM |
|---|---|---|---|---|---|
| (1) | —C$_3$H$_6$-1-Piperidine | H | -1,3-butadiene | 3,4-dichlorophenyl | 2.2* |
| (2) | —C$_3$H$_6$—N-morpholine | H | -1,3-butadiene | 3,4-dichlorophenyl | 10.8** |

*Average of several experiments.
**Average of two experiments.

CD3—Blast Chemotaxis Assay

Recombinant human MCP-1 was obtained from Peprotech (Rockey Hill, N.J.). T lymphocyte blast cells (CD3-Blasts) were generated by standard protocols (Coligan, J. E., A. M. Kruisbeek, D. H. Macgulies, E. M. Shevach, and W. Strober, editors. 1992. Current Protocols in Immunology. John Wiley and Sons, New York, 7.1.2, 7.10.1–7.10.10). Briefly, human peripheral blood mononuclear cells (PBMC) were isolated from heparinized venous blood by Percoll density gradient centrifugation (d=1.088) at room temperature. RBCs were removed by hypotonic lysis or Dextran sedimentation. Blast cells were generated by incubating 2×10$^6$ PBMC in 24-well tissue culture plates that were coated with 2.5 μg of an anti-CD3 monoclonal antibody (identified as TR66, a gift from Dr. A. Lanzivecchia; similar monoclonal antibody is HIT3a, from Parmingen #30111A) at 37° C. for 48 to 72 hours, and then transferring 12-wells to T25 or T75 flasks with RPMI (Roswell Park Memorial Institute 1640, a growth cell medium available from Gibco/RBL, Inc., N.Y.)+10% FCS (fetal calf serum)+50 units/ml IL-2. The cells are expanded and cultured for up to 3 weeks. CD3-Blast chemotaxis was assessed no sooner than 3 to 4 days after transfer to the IL-2 containing medium using a modification of a transendothelial migration assay (Carr. M. W., S. J. Roth, B. Luther, S. S. Rose, and T. A. Springer. 1994. Monocyte chemoattractant protein 1 acts as a T-lymphocyte chemoattractant. Proc. Natl. Acad. Sci. USA 91:3652–6). The endothelial cells used for this assay were the endothelial cell line ECV304, (ECV304 was from the European Collection of Animal Cell Cultures, Porton Downs, UK assession #92091712). Endothelial cells were cultured on 6.5 mm diameter Transwell culture inserts (Costar) with a 3.0 mm pore size. Culture media for ECV304 cells consisted of M199 (a cell culture medium from Gibco BRL, Inc., Gaithersburg, Md.)+10% FCS (fetal calf serum from Gibco BRL, Inc.), L-glutamine, and antibiotics (the penicillin concentration was 50 U/ml, and the streptomycin concentration was 50 ug/ml; both from Gibco, N.Y.). Assay media consisted of equal parts RPMI 1640 and M199, with 0.5% BSA (bovine serum albumin or simply RPMI 1640 with 0.5% BSA). Twenty four hours before the assay, 2×10$^5$ ECV304 cells were plated onto each insert of the 24 well chemotaxis plate and incubated at 37° C. MCP-1 (about 10 nM diluted in assay medium) with or without compounds, was added to the wells of a 24-well tissue culture plate in a final volume of 600 ml. Endothelial coated Transwells were inserted into each well and 10$^6$ CD3-Blasts were added to the top chamber in a final volume of 100 ml, with or without compounds. The plate was then incubated at 37° C. in 5% CO2/95% air for approximately 1 hour. The cells that had migrated to the bottom chamber were enumerated using flow cytometry. 500 ml of the cell suspension from the lower chamber was placed in a tube, and relative cell counts were obtained by acquiring events for a set time period of 30 seconds. This counting method was found to be highly reproducible, and enabled gating on the leukocytes and the exclusion of debris or other cells. Background migration was determined by counting cells that migrated in the absence of MCP-1 in the lower chamber. This background migration of cells per 30 second count was subtracted from the migration to MCP-1 to obtain specific migration. The percent inhibition by compounds of directed migration was determined by the following formula:

$$1 - \left[\frac{Mc}{Mo}\right]$$

where Mc=the specific migration in the presence of compound and Mo=the specific migration in the absence of compound.

Table II CD3 Chemotaxis Assay

TABLE II

CD3 BLAST CHEMOTAXIS ASSAY

| Example | X' | $R_1$ | $R_2$ | $IC_{50} \mu M$ |
|---------|------|-------|-------|------------|
| 1 | 3,4-Cl$_2$ | —C$_3$H$_6$—N-piperidine | H | 23 |

Streptococcal Cell Wall Arthritis

Streptococcal cell wall (SCW) arthritis is induced in female Lewis rats (200 gms). To induce the subacute, transient arthritis response, a highly refined preparation of streptococcal cell walls (100P, Lee Laboratories, Grayson, Ga.) is injected into the ankle joints of female Lewis rats (6 $\mu$l in Dulbecco's PBS). Twenty one days later, the animals were given an IV booster of SCW at a dose of 100 $\mu$g/rat in 0.25 mL of Dulbeccols PBS. Vehicle (0.5% hydroxypropy-lmethylcellulose and 0.2% Tween 80, 10 mL/kg) or test compounds suspended in vehicle is given one hour before the IV challenge with SCW and daily thereafter for 3 additional days. Paw volume is measured daily by mercury plethysmography. Swelling was determined by comparing paw volume at the various timepoints with an initial paw volume measurement for each rat. Percent inhibition of swelling in compound-treated rats is determined in comparison with swelling in rats treated with vehicle. Statistical power is calculated using an analysis of covariance with a contract mean comparison test (n=5–10 per experimental group).

Glucan Vasculitis Model

Pulmonary granulomatous vasculitis was induced in anesthetized, 150–200 gram male Lewis rats by intravenous infusion of 5 mg. glucan. Infusion of particulate yeast cell-wall glucan into rats results in the rapid and synchronous development of angiocentric pulmonary granulomas which are composed almost entirely of monocytes and macrophages. It has been shown previously that MCP-1 MRNA expression and MCP-1 activity in lung lavage fluid rise in association with pulmonary granuloma development, and that granuloma development is markedly attenuated in rats treated with neutralizing concentrations of anti-MCP-1 antibody. This suggests that MCP-1 plays a pivotal role in the pathogenesis of glucan-induced granulomatous vasculitis. For these studies, compound was given by oral gavage at the indicated doses one hour prior to, and then twenty-four and forty-eight hours after glucan infusion. The rats were sacrificed seventy-two hours after the glucan infusion. At the time of sacrifice, the lungs were lavaged with 6.0 mls. PBS/EDTA. Total cell counts in the recovered lavage fluid were obtained on a coulter counter, and cytocentrifuge preparations were prepared for differential cell counts. Following the lavage, the lungs were fixed with 10% neutral buffered formalin for routine processing and histological assessment of pulmonary vasculitis. The test results are shown in FIG. 1 for Example 1 compound.

Inhibition of T Cell Recruitment to Rat Skin Inflammatory Sites by Compound 1

Method of Evaluation

Inbred, approximately 200 gm, male Lewis rats were used in all experiments. Cutaneous delayed hypersensitivity (DHR) was induced as previously described (1). Briefly, rats were sensitized to KLH (Sigma Chemical Co., St. Louis, Mo.) by administering 50 $\mu$g KLH in 0.1 ml complete Freund's adjuvant (CFA; Sigma Chemical Co.) into each of 4 subcutaneous sites. After 14 days, DHR was elicited by the challenge of 5 $\mu$g KLH in PBS into multiple intradermal sites on the back. Analysis was performed 24 hours after antigen challenge. For each experiment, there were at least three groups of animals of at least four animals in each group. One group of nonsensitized, naive animals was used as a negative control and received vehicle alone (consisting of 0.5% hydroxypropylmethylcellulose/0.2% Tween 80 in water) per os at the time of challenge. As positive controls, one group of sensitized animals received alone per os at the time of KLH challenge. A third group consisted of sensitized animals that received compound suspended in vehicle per os at the time of KLH challenge.

T cell recruitment at sites of DHR was quantified using methods previously described (1–4). Briefly, rat T cells were isolated from spleen of naive adult Lewis rats by mincing the splenic tissue, removing the red cells by hypotonic lysis, and passing the cells through a nylon wool column. The cells in the effluent were highly purified (>95%) rat T cells as assessed by anti-rat CD3 (monoclonal antibody KT3, Biosource International, Camarillo, Calif.) immunoreactivity by flow cytometry. Radiolabeling was performed by suspending $5\times10^7$ T cells in 0.5 ml RPMI 1640 medium with 7.5 $\mu$Ci $^{111}$In-oxiquinoline (Amersham Corp., Arlington Hgts, Ill.) for 20 min at room temperature so that $2\times10^7$ T cells yielded approximately $0.5-2\times10^6$ cpm of $\gamma$ activity. The cells were then washed twice, resuspended in RPMI 1640 plus 10% normal rat serum, and $2\times10^7$ labeled T cells/200 gm body weight rat were injected intravenously at the time of KLH intradermal challenge. Skin challenge sites (8 mm in diameter) were counted on a $\gamma$ counter 24 hours after injection of radiolabeled T cells. Lung, liver, and spleen were also collected and counted as comparative indices for evaluation of input.

Statistical significance was determined using a paired Student's t-test. Differences between means were considered significant when P<0.05.

Results

When administered once per os at the time of antigen challenge, Compound #1 inhibited the recruitment of $^{111}$In-labeled rat T cells to skin DHR sites in a dose-dependent fashion with approximately 80% inhibition at 30 mg/kg (P<0.05) (FIG. 2).

REFERENCES

1. Issekutz, T. B., J. M. Stoltz, and P. V. D. Meide. 1988. Lymphocyte recruitment in delayed-type hypersensitivity: the role of IFN-gamma. *J. Immunol.* 140:2989–2993.
2. Issekutz, T. B. 1991. Inhibition of in vivo lymphocyte migration to inflammation and homing too lymphoid tissues by the TA-2 monoclonal antibody: a likely role for VLA-4 in vivo. *J. Immunol.* 147:4178–4184.
3. Issekutz, T. B. and A. C. Issekutz. 1991. T lymphocyte migration to arthritic joints and dermal inflammation in the rat: differing migration patterns and the involvement of VLA-4. *Clin. Immunol. Immunopatliol.* 61:436–447.
4. Issekutz, T. B. 1993. Dual inhibition of VLA-4 and LFA-1 maximally inhibits cutaneous delayed-type hypersensitivity-induced inflammation. *Am. J. Pathol.* 143:1286–1293.

The compounds of the present invention can be prepared and administered in a wide variety of routes of administration such as parenteral, oral, topical, rectal, inhalation and the like. Formulations will vary according to the route of administration selected. Examples are oral and parenteral dosage forms. Thus, the compounds of the present invention can be administered by injection, that is, intravenously, intramuscularly, intra-cutaneously, subcutaneously, intraduodenally, or intra-peritoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in a pharmaceutically acceptable carrier, such as aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water or another suitable carrier with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 mg to 200 mg, preferably about 0.5 mg to 100 mg according to the particular application and the potency of the active component. The composition can, if desired, also contain other compatible therapeutic agents.

In therapeutic use as agents for the treatment of atherosclerosis, restenosis, and immune disorders such as arthritis and transplant rejection, the compounds utilized in the pharmaceutical methods of this invention can be administered at an initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is; increased by small increments until the optimum effect under the circumstances is reached. For convenience, the total daily dosage may be divided and administered in portions during the day, if desired.

The ACAT inhibitors, HMG-COA reductase inhibitors, lipid regulators, and bile acid sequestrants utilized in the second embodiment of the present invention can be used in standard dosage amounts known in the art.

As further exemplification of the invention listed below are preferred embodiments wherein all parts are parts by weight and all temperatures are degrees Centigrade unless otherwise indicated.

EXAMPLES OF PREFERRED COMPOUNDS ARE:

Example 1

Compound 1

5-(3,4-Dichloro-phenyl)-penta-2,4-dienoic Acid (3-piperidin-1-yl-propyl)-amide-HCl mp 192–194° C.

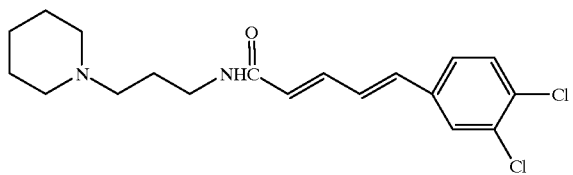

Other preferred compounds are recited below.

Example 2
5-(3,4-Dichloro-phenyl)-penta-2,4-dienoic Acid (3-morpholin-4-yl-propyl)-amide mp 130–132° C.

Example 3
5-(3,4-Dichloro-phenyl)-penta-2,4-dienoic Acid bis-(2-dimethylamino-ethyl)-amide

Example 4
5-(3,4-Dichloro-phenyl)-penta-2,4-dienoic Acid (2-diethylamino-ethyl)-amide

Example 5
5-(3,4-Dichloro-phenyl)-penta-2,4-dienoic Acid (2-piperazin-1-yl-ethyl)-amide

Example 6
5-(3,4-Dichloro-phenyl)-penta-2,4-dienoic Acid (3-dimethylamino-propyl)-amide

Example 7
5-(3,4-Dichloro-phenyl)-penta-2,4-dienoic Acid (3-diethylamino-propyl)-amide

Example 8
5-(3,4-Dichloro-phenyl)-penta-2,4-dienoic Acid (2-pyridin-4-yl-ethyl)-amide

Example 9
(2E,4E)-5-p-Tolyl-penta-2,4-dienoic Acid (3-piperidin-1-yl-propyl)-amide mp 40–50° C.

Example 10
(2E,4E)-5-(4-Methoxy-phenyl)-penta-2,4-dienoic Acid (3-piperidin-1-yl-propyl)-amide mp 69–73° C.

Example 11
(2E,4E)-5-(4-Nitro-phenyl)-penta-2,4-dienoic Acid (3-piperidin-1-yl-propyl)-amide mp 225–226° C.

Example 12
(2E,4E)-5-(4-Chloro-phenyl)-penta-2,4-dienoic Acid (3-piperidin-1-yl-propyl)-amide mp 60–62° C.

Example 13
(2E,4E)-5-Phenyl-penta-2,4-dienoic Acid (3-piperidin-1-yl-propyl)-amide mp 111–115° C.

Example 14
(2E,4E)-5-Biphenyl-4-yl-penta-2,4-dienoic Acid (3-piperidin-1-yl-propyl)-amide mp 165–168° C.

Example 15
(2E,4E)-5-Naphthalen-2-yl-penta-2,4-dienoic Acid (3-piperidin-1-yl-propyl)-amide mp 150–156° C.

Example 16
(2E,4E)-5-(3,5-Dichloro-phenyl)-penta-2,4-dienoic Acid (3-piperidin-1-yl-propyl)-amide mp 186–187° C.

Example 17
(2E,4E)-5-(2,4-Dichloro-phenyl)-penta-2,4-dienoic Acid (3-piperidin-1-yl-propyl)-amide mp 66–69° C.

Example 18
(2E/Z,4E)-5-(3,4-Dichloro-phenyl)-3-methyl-penta-2,4-dienoic Acid (3-piperidin-1-yl-propyl)-amide mp 63–70° C.

Example 19
(2E,4E)-5-(3,4-Dichloro-phenyl)-3-methyl-penta-2,4-dienoic Acid (3-piperidin-1-yl-propyl)-amide mp 165–170° C.

Example 20
(2Z,4E)-5-(3,4-Dichloro-phenyl)-3-methyl-penta-2,4-dienoic Acid (3-piperidin-1-yl-propyl)-amide mp 50–60° C.

Example 21
(2E,4E)-5-(3,4-Dichloro-phenyl)-hexa-2,4-dienoic Acid (3-piperidin-1-yl-propyl)amide mp 65–70° C.

Example 22
(2E) -5,5-Diphenyl-penta-2,4-dienoic acid (3-piperidin-1-yl-propyl)-amide mp 55–65° C.

Example 23
(2E,4E)-5-(3,4-Dichloro-phenyl)-3-phenyl-penta-2,4-dienoic Acid (3-pipereidin-1-yl-propyl)-amide mp 253–255° C.

Example 24
(2Z,4E)-5-(3,4-Dichloro-phenyl)-3-phenyl-penta-2,4-dienoic Acid (3-pipereidin-1-yl-propyl)-amide mp 85–100° C.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A method of inhibiting the binding of the monocytes chemoattractant protein-1(MCP-1) receptor in a mammal in need thereof comprising administrating to such mammal an effective inhibiting amount of a compound of Formula (I):

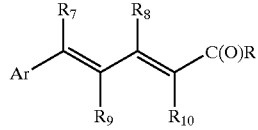

FORMULA I wherein R is any one of the following moieties:

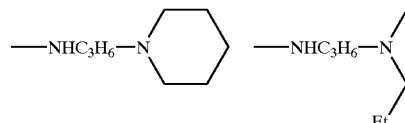

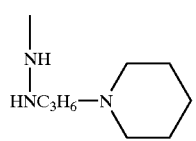

-continued

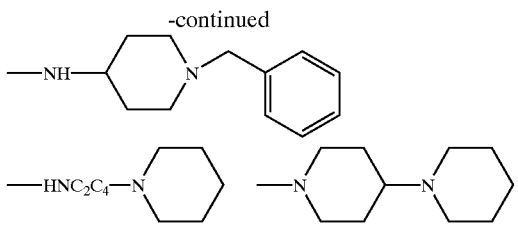

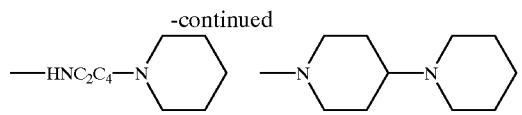

Ar can be unsubstituted or substituted phenyl, biphenyl, or naphthyl;
the substituents are defined as:
halogen,
nitro,
$CF_3$,
alkyl of from 1–12 carbon atoms;
—$(CH_2)_rOR_6$
—$(CH_2)_rNR_3R_4$
—$(CH_2)_rCONR_3R_4$
—$(CH_2)_rC(O)OR_6$ or
—$(CH_2)_r$—$SO_2$—$OR_6$;

$R_3$, $R_4$, and $R_6$, are independently selected from the group hydrogen and lower alkyl;
r=0–4;
$R_7$, $R_8$, $R_9$ and $R_{10}$ each independently are hydrogen, or lower alkyl, or pharmaceutically acceptable salts thereof.

2. The method of claim 1 wherein Ar is naphthyl.
3. The method of claim 1 wherein Ar is phenyl and the substiuents are chloro.
4. The method of claim 1, wherein $R_7$, $R_8$, $R_9$ and $R_{10}$ are hydrogen.
5. A method of inhibiting the binding of the monocytes chemoattractant protein-1 (MCP-1) receptor in a mammal in need thereof comprising administrating to such mammal an effective inhibiting amount of a compound of the formula:

Ar-CH=CHCH=CHCOR wherein R is any one of the following moieties:

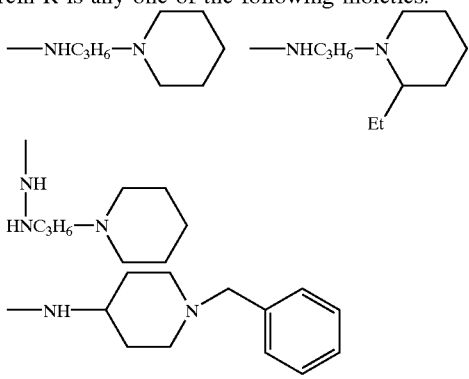

Ar can be unsubstituted or substituted phenyl, biphenyl, or naphthyl;
the substituents are defined as:
halogen,
nitro,
$CF_3$,
alkyl of from 1–12 carbon atoms;
—$(CH_2)_rOR6$
—$(CH_2)_rNR_3R_4$
—$(CH_2)_rCONR_3R_4$
—$(CH_2)_rC(O)OR_6$ or
—$(CH_2)_r$—$SO_2OR_6$;

$R_3$, $R_4$, and $R_6$ are independently selected from the group hydrogen and lower alkyl; and
r=0–4, and pharmaceutically acceptable salts thereof.

6. The method of claim 1, wherein said compound is (2E, 4E)-5-p-Tolyl- penta-2,4-dienoic acid (3-piperidin-1-yl-propyl) amide.
7. The method of claim 1, wherein said compound is (2E, 4E)-5-(4- methoxy-phenyl)-penta-2,4-dienoic acid (3-piperidin-1-yl-propyl) amide.
8. The method of claim 1, wherein said compound is (2E, 4E)-5-(4-nitro- phenyl)-penta-2,4-dienoic acid (3-piperidin-1-yl-propyl) amide.
9. The method of claim 1, wherein said compound is (2E, 4E)-5-(4-chloro- phenyl)-penta-2,4-dienoic acid (3-piperidin-1-yl-propyl) amide.
10. The method of claim 1, wherein said compound is (2E, 4E)-5-phenyl- penta-2,4-dienoic acid (3-piperidin-1-yl-propyl) amide.
11. The method of claim 1, wherein said compound is (2E, 4E)-5-biphen-4-yl-penta-2,4-dienoic acid (3-piperidin-1-yl-propyl) amide.
12. The method of claim 1, wherein said compound is (2E, 4E)-5-naphthalen-2-yl-penta-2,4-dienoic acid (3-piperidin-1-yl-propyl) amide.
13. The method of claim 1 or 5, wherein said compound is 5-(3, 4-dichloro- phenyl)-penta-2,4-dienoic acid (3-piperidin- 1-yl-propyl) amide.
14. The method of claim 1, wherein said compound is (2E, 4E)-5-(3, 5- dichloro-phenyl)-penta-2,4-dienoic acid (3-piperidin- 1-yl-propyl) amide.
15. The method of claim 1, wherein said compound is (2E, 4E)-5-(2,4- dichloro-phenyl)-penta-2,4-dienoic acid (3-piperidin- 1-yl-propyl) amide.

* * * * *